United States Patent
Scheer (10) Patent No.: US 7,892,593 B2
(45) Date of Patent: Feb. 22, 2011

(54) PROCESS FOR COATING A SUBSTRATE

(76) Inventor: Ingo Werner Scheer, 6455 La Jolla Blvd., La Jolla, CA (US) 92037

( * ) Notice: Subject to any disclaimer, the term of this patent is extended or adjusted under 35 U.S.C. 154(b) by 1275 days.

(21) Appl. No.: 11/476,493

(22) Filed: Jun. 27, 2006

(65) Prior Publication Data

US 2008/0286440 A1 Nov. 20, 2008

(51) Int. Cl.
B05D 1/02 (2006.01)
B05D 5/02 (2006.01)
B05B 1/00 (2006.01)

(52) U.S. Cl. .................. 427/2.1; 427/2.24; 427/2.25; 427/421.1; 239/301

(58) Field of Classification Search ......... 427/2.1–2.31, 427/532, 421.1
See application file for complete search history.

(56) References Cited

U.S. PATENT DOCUMENTS

| 4,601,921 A * | 7/1986 | Lee ............................. 427/240 |
| 4,733,665 A | 3/1988 | Palmaz |
| 6,010,081 A * | 1/2000 | Park et al. .................... 239/301 |
| 6,143,370 A | 11/2000 | Panagiotou |
| 6,439,243 B2 | 8/2002 | Laughlin |
| 6,861,088 B2 | 3/2005 | Weber |
| 7,125,577 B2 * | 10/2006 | Chappa ..................... 427/2.24 |
| 2005/0158449 A1 | 7/2005 | Chappa |
| 2007/0212477 A1 * | 9/2007 | Feng et al. ................... 427/2.1 |

FOREIGN PATENT DOCUMENTS

| WO | WO 00/58014 A1 | 10/2000 |
| WO | WO 2005/061119 A1 | 7/2005 |

OTHER PUBLICATIONS

M. M. Ribeiro and J. H. Whitelaw. Coaxial jets with and without swirl. Journal of Fluid Mechanics, 96:769-795, 1980.

* cited by examiner

Primary Examiner—Timothy H Meeks
Assistant Examiner—Cachet I Sellman (57) ABSTRACT

A method to coat a substrate for the formation of coatings having a desired surface morphology is provided, wherein the roughness and the total surface area of the coating can be varied during the coating process. The method of the present invention comprises the steps of generating droplets from a coating composition, transporting the droplets to the substrate and depositing a majority of the droplets on the substrate.

21 Claims, 8 Drawing Sheets

PROCESS FOR COATING A SUBSTRATE

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION

The present invention relates to an apparatus and method for applying a coating to at least a portion of a substrate having desired surface properties. In particular, the invention relates to a method for producing polymer coatings with various morphologies on medical implants, such as stents.

Coatings are often applied to medical implants, such as pacemakers, vascular grafts, catheters, stents, heart valves, tissues or sensors to have desired effects and increase their effectiveness. These coatings may deliver a therapeutic agent to the lumen that reduces smooth muscle tissue proliferation or restenosis and may comprise a polymer carrier. Furthermore, implants may be coated to improve surface properties such as lubriciousness, to achieve enhanced biocompatibility and to control the timing and rate of release of the therapeutic agent being delivered. Balloon delivery systems, stent grafts and expandable stents are specific examples of implants that may be coated and inserted within the body. Stents such as described in U.S. Pat. No. 4,733,665 are tiny, expandable mesh tubes supporting the inner walls of a lumen used to restore adequate blood flow to the heart and other organs.

Figure 1A:
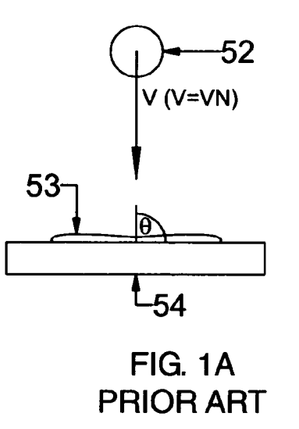
FIG. 1A (Prior Art) is a schematic representation of an droplet impact onto a substrate with an normal impact angle (90 degrees)

Such coatings have been often applied to the surface of an implant by spray coating. An atomizing device including an orifice and an internal fluid passage leading to said orifice is typically placed perpendicular to the longitudinal axis of the substrate to be coated. The droplets 52 generated by the atomizing device are expelled through the orifice and the majority of the droplets hit the surface of substrate 54 at an impact angle of approximately $\theta=90$ degrees with a comparatively high impulse force resulting in a dense coating splat 53 as shown in FIG. 1A.

The comparatively high coating compaction of the produced coating may however result in an inhomogeneous coating thickness and cracks. In addition, it may be difficult to produce porous coatings, which can be used in medical implants as reservoirs for the retention of therapeutic agents and may be desirable to enhance tissue ingrowth and tissue healing.

Also, conventional coating methods, such as described in U.S. Pat. No. 6,143,370, may not allow the coating of a stent so that the morphology of the coating layer can be changed instantaneously, which may be desirable to accommodate the need for different elution profiles as may be required by the medical application.

OBJECT OF THE INVENTION

Accordingly, there is a need for an inexpensive and flexible way of coating substrates so that a desired surface morphology can be produced to accommodate the need for different therapeutic agents.

The main object of the invention is to provide a cost-effective and flexible method to form a polymer coating on a substrate having desired surface properties in terms of surface roughness and surface area.

Another object is to allow immediate adjustment of coating properties so that a variable coating thickness and morphology along the surface of the substrate can be produced.

It is still another object to minimize coating compaction and to increase porosity and surface area of the coating.

These and additional features and advantages of the invention will be more readily apparent upon reading the following description of exemplary embodiments of the invention and upon reference to the accompanying drawings herein.

BRIEF SUMMARY OF THE INVENTION

The method of the invention provides an improved process for the formation of coatings having a desired surface morphology. The coatings may include a polymer carrier and a therapeutic substance. Coatings formed by the process of the invention can be designed to exhibit different properties according to the particular requirements. For example, the porosity, the roughness and the total surface area of the coating can be varied during the spray run. The mass diffusion rates through the surface may be controlled by either increasing or decreasing the surface area of the coating and the porosity in the process of the present invention. Thus, the surface area and porosity may be varied to provide selective coating properties of the coating layer along the surface of the substrate.

The process of the present invention comprises the steps of generating droplets from a coating composition, transporting the droplets to the substrate, so that the majority of the droplets have a tangential velocity component in relation to the substrate and depositing the droplets on the substrate so that the impact angle of the majority of the droplets is less than 80 degrees.

The droplets may be deposited at an impact angle of preferably less than 80 degree so that a coating with a certain surface area and porosity is obtained. The droplet generation and/or transportation process may be controlled to change the impact angle, defined as the angle between the direction vector of the droplet and the surface of the substrate, of the generated droplets to provide selective surface properties.

SUMMARY

In one embodiment of the present invention, a method to apply a coating to an implant, using an atomizer to disintegrate the coating composition into droplets is provided. The method comprises the steps of tilting the atomizer in relation to the implant so that the angle between the spray axis and the surface of the implant is less than 80 degrees, generating droplets from a coating substance, transporting the droplets to the implant so that the majority of the droplets have a tangential velocity component in relation to the surface of the implant, and depositing the droplets on the implant so that the impact angle of the majority of the droplets is less than 80 degrees. The method may further comprise the step of changing the angle between the spray axis and the surface of the implant during the coating process in order to vary the morphology of the coating layer.

In a next embodiment, a method to apply a coating to a substrate using means to disintegrate the coating composition into droplets and means to generate a vortical gas flow field to transport the droplets to a substrate having a defined swirl intensity is provided. The method comprises the steps of forming droplets from a coating substance, defining the swirl intensity and generating a vortical gas flow field, transporting the droplets in said gas flow field to the substrate so that the majority of the droplets have a tangential velocity component in relation to the surface of the substrate, and depositing the droplets on the substrate so that the impact angle of the majority of the droplets is less than 80 degrees. In one or more embodiments, the means to generate a vortical gas flow field may comprise a conduit with at least a first and a second gas inlet, and at least one gas inlet is used to induce swirl motion in the gas flow. Also, the means to disintegrate the coating composition may comprise at least one atomizer, such as a twin-fluid nozzle, which provides a vortical gas flow. In addition, the swirl intensity can be changed by adjusting the ratio between axial gas flux of swirl momentum and axial gas flux of axial momentum. The method may further comprise the step of changing the swirl intensity during the coating run in order to vary the morphology of the coating along the surface of the substrate, wherein the swirl intensity of the gas flow field is preferably between 0.01 and 1.0.

In a further embodiment, a method to apply a coating to a substrate using means to generate droplets from a liquid having at least one exit aperture and means to generate a gas flow field having at least one entrance aperture is provided. The method comprises the steps of forming droplets from a coating substance, generating a gas flow field to direct the droplets to the substrate so that the majority of the droplets comprise a tangential velocity component in relation to the surface of the substrate, positioning the substrate between said exit aperture and said entrance aperture, and depositing the droplets on the surface of the substrate so that the impact angle of the majority of the droplets is less than 80 degrees.

In one or more embodiments, the droplets may be generated through vibration and/or by electrostatic energy. The gas flow field may be produced by means of a suction device. The substrate can be supported by a fixture and the entrance aperture may be located within the fixture. In addition, the entrance aperture can be positioned at an offset distance from the spray axis of the droplet generation device and the position of the entrance aperture can be changed during the application of the coating in order to vary the morphology of the coating layer. Also, the entrance aperture may be tilted in relation to the spray axis. Further, the tilt angle of the entrance aperture can be changed during the application of the coating in order to vary the morphology.

In an alternative embodiment, a method to apply a coating to an implant is provided. The method comprises the steps of generating droplets from a coating substance, transporting the droplets to the implant so that the majority of the droplets have a tangential velocity component in relation to the surface of the implant, and depositing the droplets on the implant so that the impact angle of the majority of the droplets is less than 80 degrees.

In yet another embodiment, a method to apply a coating to a substrate using means to generate droplets from a liquid having at least one exit aperture and means to generate a gas flow field having at least one entrance aperture is provided. The method comprises the steps of forming droplets from a coating substance having a velocity of less than 5 m/s in proximity of the exit aperture, generating a gas flow field to direct the droplets to the substrate, positioning the substrate between said exit aperture and said entrance aperture, and depositing the droplets on the surface of the substrate.

BRIEF DESCRIPTION OF THE SEVERAL VIEWS OF THE DRAWINGS

The accompanying drawings, which are incorporated herein and form a part of the specification, illustrate the embodiments of the present invention and together with the description, serve to explain the principles of the invention. In the drawings.

DETAILED DESCRIPTION

Further aspects of the invention will become apparent from consideration of the drawings and the ensuing description of preferred embodiments of the invention. A person skilled in the art will realize that other embodiments of the invention are possible and that the details of the invention can be modified in a number of respects, all without departing from the inventive concept. Thus, the following drawings and description are to be regarded as illustrative in nature and not restrictive. Further features and advantages of the present invention, as well as the structure and operation of various embodiments of the present invention, are described in detail below with reference to the accompanying drawings.

Figure 2:
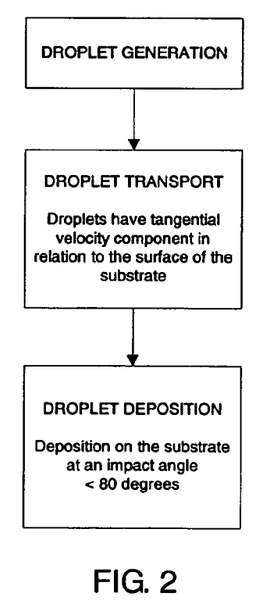
FIG. 2 is a flow chart of the coating method of the present invention.
Figure 8:
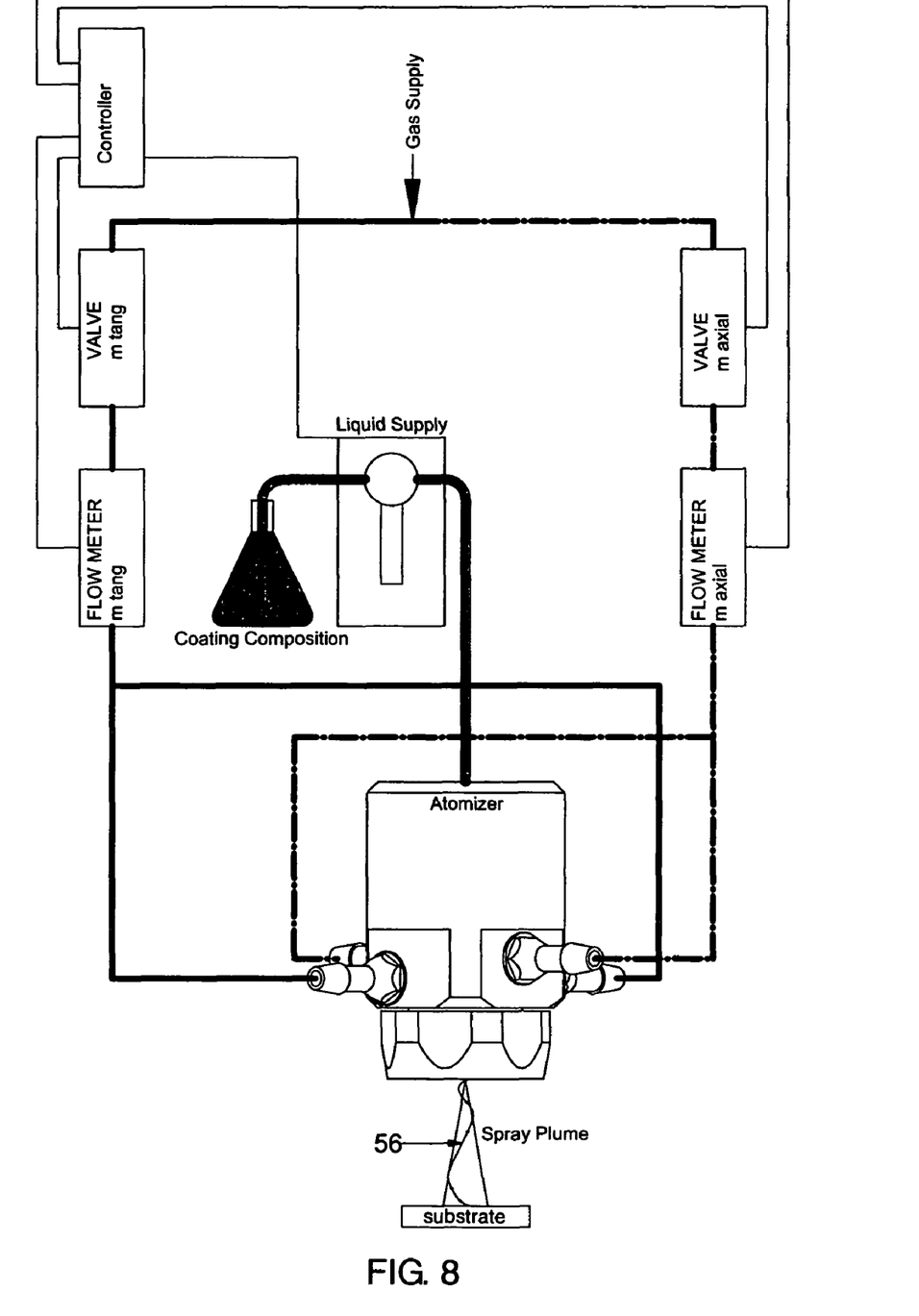
FIG. 8 is a diagrammatic representation of an exemplary coating setup.
Figure 9:
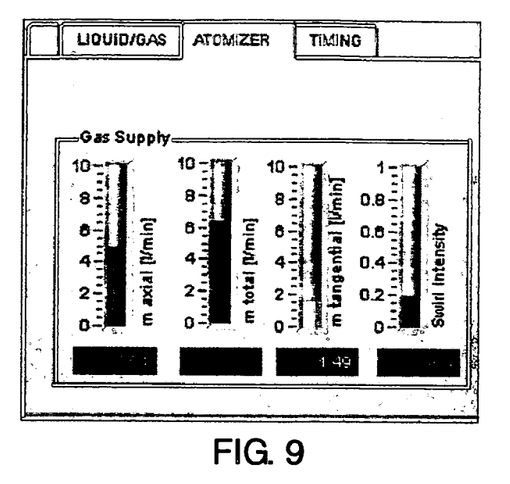
FIG. 9 is a portion of a screen dump of the software used to control the swirl intensity.
Figure 10:
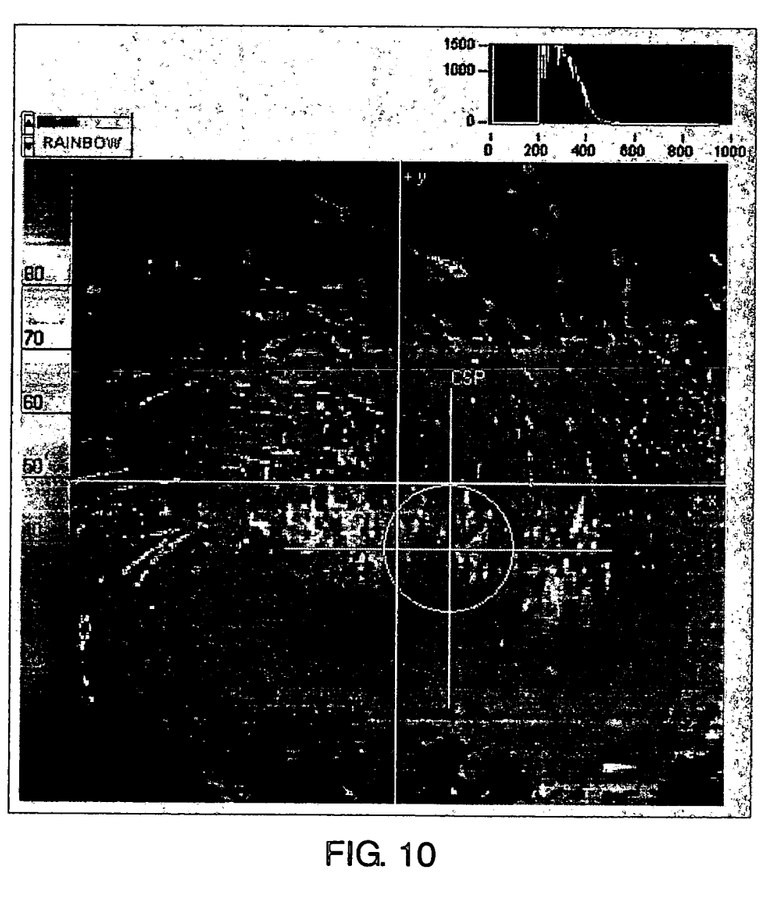
FIG. 10 is a spatial droplet distribution of a spray pattern at a swirl intensity of 0.3.

Referring now to FIG. 2, the method to apply a coating layer to a substrate, such as a stent, having a desired roughness and porosity comprises the steps of generating droplets from a coating composition, transporting the droplets to the substrate so that the majority of the droplets have a tangential velocity component in relation to the surface of the substrate and depositing the droplets on the substrate so that the impact angle of the majority of the droplets is less than 80 degrees. The droplet generation and transportation step can be controlled as described in detail in FIG. 8 to fine tune surface properties of the substrate to be coated.

The substrate is preferably an implant and may include pacemakers, vascular grafts, catheters, stents, heart valves, tissues, sensors and the like.

The coating composition may comprise a solvent, a polymer, and a therapeutic substance. The therapeutic substance may include, but is not limited to, proteins, hormones, vitamins, antioxidants, DNA, antimetabolite agents, anti-inflammatory agents, anti-restenosis agents, anti-thrombogenic agents, antibiotics, anti-platelet agents, anti-clotting agents, chelating agents, or antibodies. Examples of suitable polymers include, but are not limited to, synthetic polymers including polyethylen (PE), poly(ethylene terephthalate), polyalkylene terepthalates such as poly(ethylene terephthalate) (PET), polycarbonates (PC), polyvinyl halides such as poly(vinyl chloride) (PVC), polyamides (PA), poly(tetrafluoroethylene) (PTFE), poly(methyl methacrylate) (PMMA), polysiloxanes, and poly(vinylidene fluoride) (PVDF); biodegradable polymers such as poly(glycolide) (PGA), poly(lactide) (PLA) and poly(anhydrides); or natural polymers including polysaccharides, cellulose and proteins such as albumin and collagen. The coating composition can also comprise active agents, radiopaque elements or radioactive isotopes. The solvent is selected based on its biocompatibility as well as the solubility of the polymer. Aqueous solvents can be used to dissolve water-soluble polymers, such as Poly (ethylene glycol) (PEG) and organic solvents may be used to dissolve hydrophobic and some hydrophilic polymers. Examples of suitable solvents include methylene chloride, ethyl acetate, ethanol, methanol, dimethyl formamide (DMF), acetone, acetonitrile, tetrahydrofuran (THF), acetic acid, dimethyle sulfoxide (DMSO), toluene, benzene, acids, butanone, water, hexane, and chloroform. For the sake of brevity, the term solvent is used to refer to any fluid dispersion medium whether a solvent of a solution or the fluid base of a suspension, as the invention is applicable in both cases.

Figure 1B:
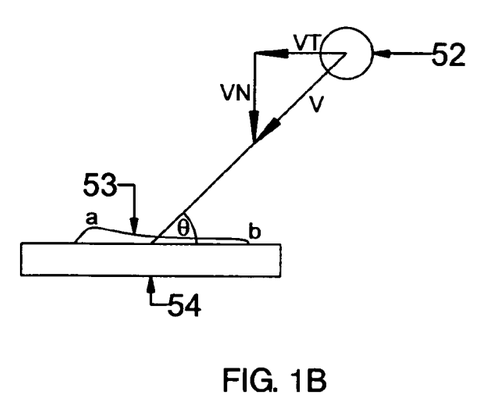
FIG. 1B is a schematic representation of a droplet impact onto a substrate at an angle <80 degrees.

FIG. 1B is a schematic of a droplet impact on a substrate according to the method of the present invention. The impact velocity V of the droplet 52 comprises a normal velocity component VN and a tangential velocity component VT resulting in an off normal impact angle θ between droplet and substrate surface. The tangential velocity component VT promotes droplet spreading over the substrate 54 rather than impacting on it. An asymmetric splat morphology is expected to occur because VT contributes to the spreading of unsolidified materials toward point a. If the spray angle is decreased, especially for α less than 45 degrees, and the tangential velocity component VT is increased, porosity and roughness of the coating increase.

Figure 3:
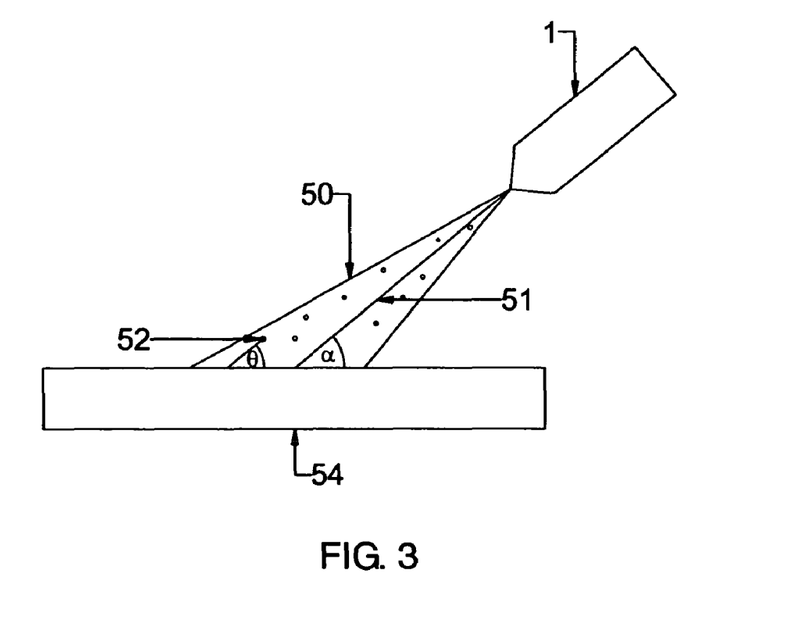
FIG. 3 is a spray coating setup of a substrate (atomizer tilted with respect to substrate)

In one exemplary embodiment as shown in FIG. 3, atomizer 1 is tilted in relation to the substrate so that the spray angle α between the spray axis 51 and the surface of the substrate is less than 80 degrees. A twin-fluid atomizer is preferably used to disintegrate the liquid to be atomized. In operation, liquid is supplied to the liquid inlet, travels through the liquid path and exits the atomizer orifice. Gas, which is fed in the gas inlet, breaks up the liquid into fine droplets when it exits the gas orifice and directs the droplets to the substrate. By tilting the atomizer in relation to the substrate droplets are generated having a tangential velocity component in relation to the surface of the substrate and the majority of droplets are deposited on the substrate 54 at an impact angle θ of less than 80 degrees.

Figure 7A:
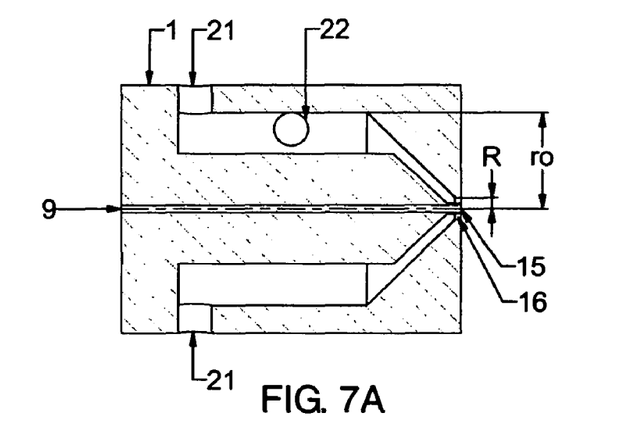
FIG. 7A is a cross sectional view of a twin-fluid atomizer having radial and tangential gas inlets.
Figure 7B:
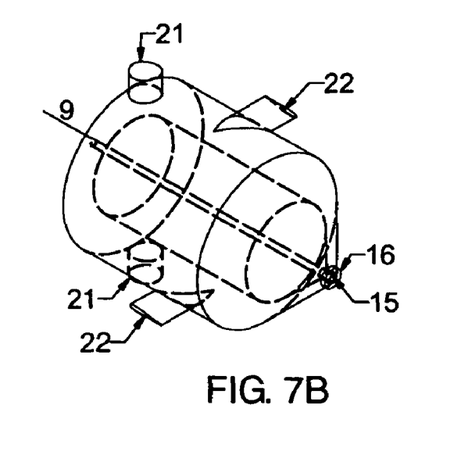
FIG. 7B is a perspective view of the gas conduit of the atomizer of FIG. 7A.

Although a twin-fluid atomizer, such as depicted in FIG. 7, is preferably used in this embodiment, it is to be understood that the principles of the present invention may be applied to other nozzle types and geometries as well, including atomizers that employ electrostatic or ultrasonic energy, for example. Dispensing and atomization systems incorporating multiple nozzles and/or atomizer assemblies of a single configuration or differing configurations may incorporate the principles of the present invention.

In order to change the surface properties such as roughness and porosity of the coating layer, the impact angle θ of the droplets may be varied by increasing or decreasing the angle α between spray axis 51 of the atomizer and substrate 54 during the coating process.

Figure 4:
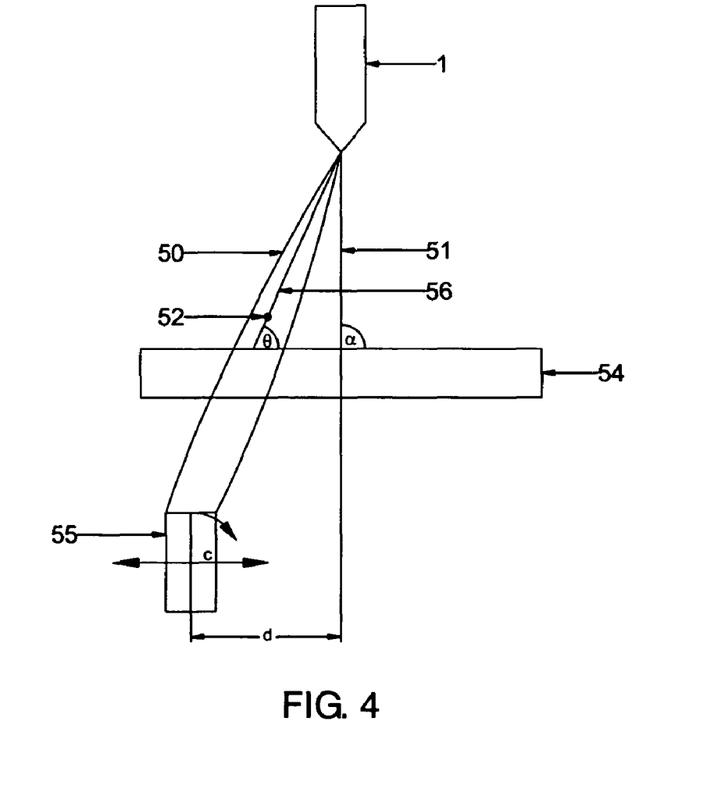
FIG. 4 is a is a spray coating setup of a substrate (suction device positioned at an offset distance with respect to atomizer)

The following exemplary embodiment is suitable if a coating having a comparatively low compaction and an increased porosity is desired. A low droplet velocity of preferably less than 5 m/s and a comparatively small droplet size minimize the droplet impulse during the coating process and prevent compaction of the coating layer. Referring to FIG. 4, an atomizer 1, (preferably an ultrasonic atomizer), an entrance aperture of a suction device 55 and a substrate 54 located there between are depicted. The atomizer 1 is positioned above the substrate and is located perpendicular or is tilted in relation to the surface of the substrate. The entrance aperture of the suction device 55, which is preferably located underneath the substrate may have an offset distance d from the spray axis 51 and may be tilted towards atomizer 1 to increase the efficiency of the coating process. The suction device may comprise an ejector having a suction capacity between 5 to 25 l/min, which is connected to the entrance aperture of the suction device 55.

In operation, a coating composition is supplied to the ultrasonic atomizer and is broken-up into fine droplets at an operation frequency of approximately 130 kHz. Droplets having a size of less than 20 µm and comparatively low droplet velocities of less than 5 m/s are produced in the proximity of the liquid orifice. The generated droplets are transported from the atomizer orifice to the substrate 54 by gravity and/or by the gas stream produced by the suction device. By positioning the entrance aperture of the suction device 55 at an off centered position at a distance d from the spray axis, tangential velocity components are generated in relation to substrate 54 and the majority of the transported droplets 52 are deposited under an impingement angle of less than 80 degrees.

The impingement angle may be changed during the coating process by altering the position or the tilt angle of the entrance aperture of the suction device. The coating properties in terms of roughness and porosity can be therefore varied along the surface of the substrate.

Figure 5:
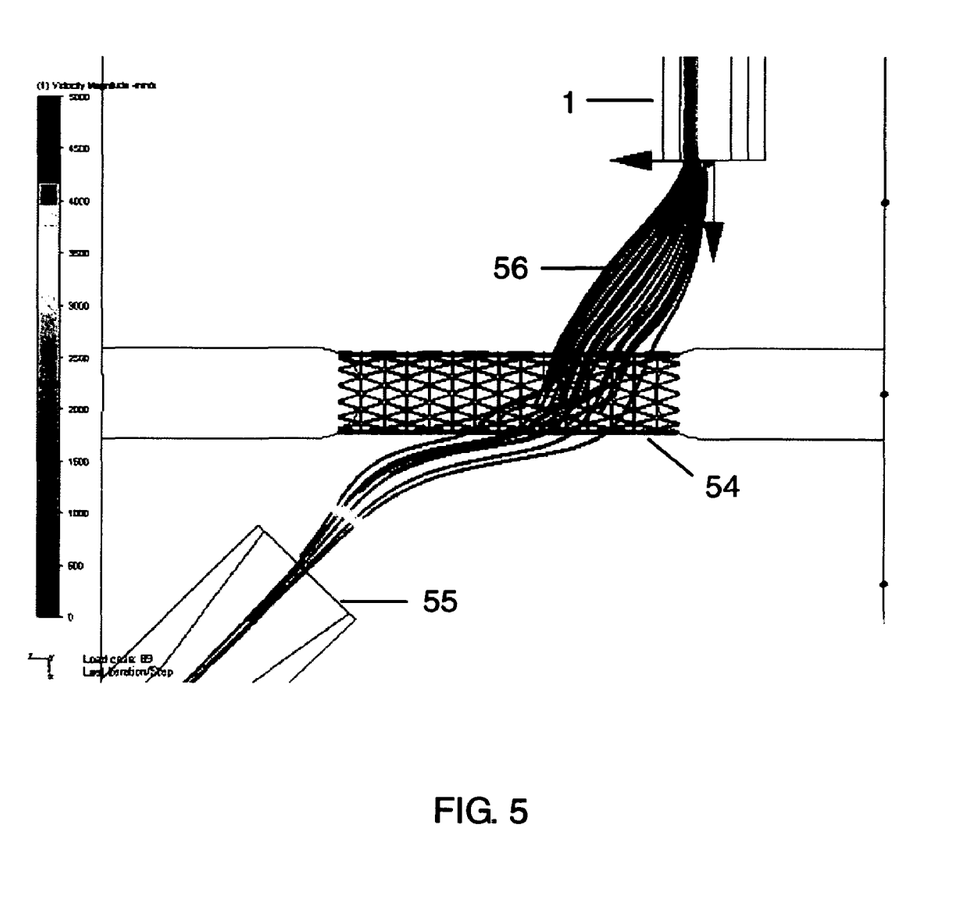
FIG. 5 is a Computational Fluid Dynamics (CFD) simulation of a stent coating process visualizing the droplet trajectories (suction device positioned at an offset distance/angle with respect to atomizer)
Figure 6:
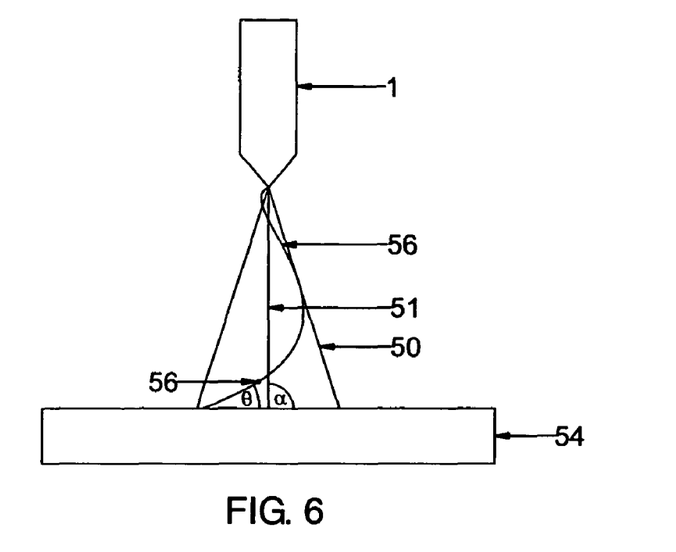
FIG. 6 is a spray coating setup of a substrate comprising a vortical flow (atomizer positioned perpendicular to substrate)

Referring to FIG. 5, a Computational Fluid Dynamics (CFD) simulation of a droplet transport and deposition process on a stent is illustrated. The volume model consists of an atomizer orifice 1, an entrance aperture 55 of a suction device and a stent 54 placed there between. The stent is supported by a holding device and located approximately 15 mm downstream from the atomizer orifice. The entrance aperture 55 of the suction device is placed at a distance of approximately 8 mm from the stent. The atomizer may also be tilted towards the entrance aperture to improve the efficiency of the process. The trajectories 56 were simulated for droplets having a diameter of approximately 18 µm. The droplets are transported from the atomizer orifice to the stent by gravity and by the gas flow field generated by the suction device. In order to direct the droplets to the stent and to deposit them at an impingement angle of less than 80 degrees a suction with a flow rate of 10 l/min was generated. Depending on the size of the substrate and the position of the entrance aperture, the suction capacity may vary between 5 and 25 l/m in. A second low velocity gas flow field may be produced at the atomizer orifice to improve process stability and to prevent deflection of the droplets, which may be caused by the air flows within the coating chamber.

A further exemplary embodiment of the present invention is depicted in FIG. 6. Atomizer 1 is preferably located perpendicular to the surface of the substrate 54. Droplets are generated from a coating composition and a gas flow field comprising a vortex is produced to direct the generated droplets to the substrate 54. Various atomizers including, but not limited to, devices employing pneumatic, electrostatic or ultrasonic energy may be used to disintegrate the fluid to be atomized. Such devises may also comprise means to generate a gas flow field with a vortex, which can include swirl inserts.

Referring to FIG. 8, an exemplary coating setup comprising atomizer, liquid and gas supply, proportion valves and flow meter arrangements for axial and tangential gas flow are provided.

By way of example, the twin-fluid atomizer of FIG. 7 is used to atomize a liquid composition through pressurized gas, provided, for example, by a compressor or by a pressurized container. Atomizer 1 comprises a liquid path extending from liquid inlet 9 to liquid orifice 15. The pressurized gas is fed through gas inlets 21 and 22 into gas conduit 6 having a radius ro and expelled through annular gap 16 having a radius R. A perspective view of gas conduit 6 depicting the position of the two inlets 21 for axial gas flow and the two tangential gas inlets 22 used to induce swirl motion into the axial gas flow is shown in FIG. 7B.

As shown in FIG. 8, the spray axis of the atomizer is located perpendicular to the surface of the substrate and positioned on the same plane. The distance between the atomizer tip and the substrate may range between 10 and 60 mm and is preferably 20 mm. The liquid inlet of the atomizer is connected to a liquid supply source. A syringe pump may be used to feed the coating composition into the atomizer. The compressed gas is fed into valves, which regulate the axial and tangential gas flow. Gas mass flows (m axial, m tang) are measured, respectively, by means of a thermal mass flow meter.

A software, developed with LabView (NI, Austin, Tex., USA) by the inventor of the present invention, is used to control the swirl intensity, the axial gas mass flow rate m axial and the tangential gas mass flow rate m tang. FIG. 9 is a portion of the Graphical User Interface of the control software displaying the current values for total flow, axial flow, tangential flow and swirl intensity. The swirl intensity of the gas can be varied instantaneously by regulating the axial and tangential gas ratio during the coating process. The impingement angle and the droplet trajectory can be thereby controlled to produce desired coating properties in terms of roughness and porosity along the surface of the substrate.

The degree of swirl is described with non-dimensional criterion S—swirl intensity or swirl number defined as a number representing axial flux of swirl momentum $G_\theta$ divided by axial flux of axial momentum $G_x$, multiplied by the nozzle radius R.

$$S = \frac{G_\theta}{RG_x}$$

The swirl intensity S is expressed by the following equation and obtained by integration of axial U and tangential W gas velocity profiles where r is the radial distance and ρ is the density as described by Ribeiro and Whitelaw.

$$S = \frac{\int_0^R \overline{\rho}\,\overline{U}\,\overline{W} r^2 dr}{R\int_0^R \overline{\rho}\left(\overline{U}^2 - \frac{1}{2}\overline{W}^2\right) r dr}$$

To allow immediate control of the swirl intensity S and the related tangential velocity component during the coating process, the swirl number can be related to the measured total gas mass flow rate $m_{tot}$ and the tangential mass flow rate $m_{tang}$. The value ro is the axial radius of the gas conduit in which the tangential gas flow is introduced, R is the nozzle exit radius and $A_t$ is the total area of the two tangential inlets.

$$S = \frac{\pi roR}{A_t}\left(\frac{m_{tang}}{m_{tot}}\right)^2$$

By controlling $m_{tot}$ and $m_{tang}$ the swirl intensity S can be changed. In operation, the desired swirl number and the total gas flow are entered by the operator. Axial gas mass flow is supplied through two symmetric inlets 21 and swirl motion is imparted to the annular flow by means of two tangential inlets 22. The gas flux comprising swirl motion is expelled through annular gap 16. A gas flow with an angular momentum is generated, resulting in a flow field with axial and tangential velocity components and increased shear forces at the atomizer orifice. The liquid flows through the liquid tube to the atomizing end, exits the liquid orifice 15 and is broken up by the atomizing air into very fine droplets having a tight droplet size distribution.

By generating an angular momentum an improved atomization of the liquid and a stabilized spray with minimized pulsation is obtained resulting in a homogeneous spatial droplet size distribution in the center of the pattern, as shown in FIG. 10.

Although some embodiments are shown to include certain features, the applicant specifically contemplate that any feature disclosed herein may be used together or in combination with any other feature on any embodiment of the invention. It is also contemplated that any feature may be specifically excluded from any embodiment of an invention. Many variations of the invention will occur to those skilled in the art. Some variations include suction devices having different geometries and which are operated at various suction flow rates depending on the particular coating setup and on the shape of the coating target. Various atomizing devices, such as single fluid nozzles, ultrasonic nozzles, electrostatic nozzles or twin-fluid nozzles, may be used to atomize the coating composition. They may also include means to support the droplet transportation and deposition process. All such variations are intended to be within the scope and spirit of the invention.

The following examples are presented to illustrate the advantages of the present invention. These examples are not intended in any way otherwise to limit the scope of the disclosure.

Stents (manufactured by STI, Israel) having a diameter of 2 mm and a length of 20 mm were coated using two different polymer compositions. In example 1 the swirl intensity has been varied between 0 and 0.6 and in example 2 the swirl intensity was set to 0.3.

The stents were mounted on a holding device as described in U.S. Pat. App. No. 60/776,522 incorporated herein as a reference. The atomizer of FIG. 7 was used to disintegrate the coating composition into fine droplets and apply the coating to the stents. Although a twin-fluid atomizer was used in the following examples, it is to be understood that the principles of the present invention may be applied to other atomizing devices as well. Dispensing and atomization systems incorporating multiple nozzles and/or atomizer assemblies of a single configuration or differing configurations may incorporate the principles of the present invention.

For best results, the atomizer may be aligned in relation to the stent so that the spray axis of the atomizer is perpendicular to the rotation axis of the stent and both axes are in the same plane. The atomizer orifice is preferably positioned at a distance of approximately 12 to 35 mm from the outer surface of the stent.

The liquid inlet of the atomizer is connected to a liquid supply source. A syringe pump (Hamilton Inc., Reno, Nev., USA) which is operated at a constant flow rate is preferably used to feed the coating substance to the atomizer. The compressed gas is fed into valves, which regulate the axial and tangential gas flow. Gas mass flows (m axial, m tang) are measured, respectively, by means of a thermal mass flow meter (TSI, Shoreview, Minn., USA).

The tangential component of velocity vt induced during the droplet generation and/or transportation process is responsible for the deposition of the droplets at an impact angle of less than 80 degrees resulting in a coating having a desired roughness and porosity. It can be varied during the coating process by changing the swirl intensity to allow a variable coating thickness along the surface of the substrate. A PC based controller is used to adjust the swirl intensity by regulating the axial gas mass flow rate m axial and the tangential gas mass flow rate m tang.

The flow rate of the coating solution may range from about 0.5 ml/h to 50 ml/h. The atomizer can disintegrate the coating solution into fine droplets at an atomizing pressure ranging from about 0.3 bar to about 1.5 bar. In order to achieve a fine atomization, the atomizer is preferably operated at a total gas flow rate of 6.2 l/min at 0.8 bar atomizing pressure.

Before exposing the substrate to the spray, it is important to make sure that the droplet generation and transportation process is stable. The spraying process may be monitored using an optical pattemator in order to ensure that the spatial droplet distribution of the generated spray plume is in the desired limits as described in U.S. Pat. App. No. 60/674,005 incorporated by reference herein.

During the application of the coating solution, rotary motion is transmitted to the stent to rotate the stent about its central longitudinal axis. The rotation speed can be from about 5 rpm to about 250 rpm. By way of example, the stent may rotate at 130 rpm. The stent is translated along its central longitudinal axis along the atomizer. The translation speed of the stent can be from about 0.2 mm/s to 8 mm/s. When applying the coating solution, the translation speed is preferably 0.5 mm/s. The stent can be moved along the atomizer one time to apply the coating in one pass or several times to apply the coating in several passes. Alternatively, the atomizer may be moved one time or several times along the stent length.

The stents may remain mounted on the holding device to allow drying of the coating and subsequent inspection. One skilled in the art can appreciate that drying may be accomplished in a variety of ways based on the coating formulation used.

Example I

Several stents were coated according to the process of the present invention. A poly(vinylidene fluoride) PVDF HFP copolymer with a monomer composition of 80% vinylidene fluoride and 10% hexaflouropropylene (Solvay Advanced Polymers, Houston, Tex., USA) was used to coat the stents. The coating solution was prepared by dissolving the polymers in acetone, at five weight percent. Both the inside and the outside surfaces of the stents were coated. Care was taken so that the stents were coated at the same operating conditions. The swirl intensity was precisely adjusted to examine its influence on the resulting surface properties. Several scanning electron microscope (SEM) images were taken to visualize the surface morphology at different swirl intensities.

Figure 11A:
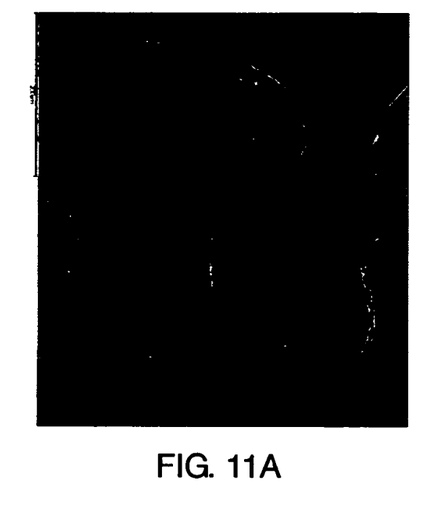
FIG. 11A is a SEM image of a portion of a stent at a swirl number of 0.

Stent #1 was coated at a swirl intensity of 0. The coating was applied according to the schematic representation of FIG. 1A so that the majority of the droplet hit the surface at an impact angle of about 90 degrees. FIG. 11A shows a portion of a coated stent having a smooth compacted coating with an inhomogeneous thickness around the struts due to an increased coating accumulation on the outer circumferential surface of the stent.

Figure 11B:
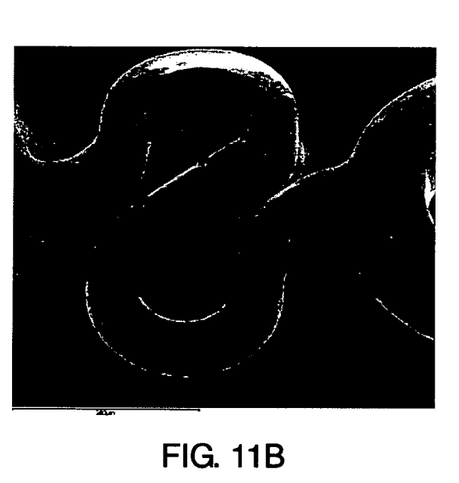
FIG. 11B is a SEM image of a portion of a stent at a swirl number of 0.3.

Stent #2 was coated at a swirl intensity of 0.3 according to the schematic representation of FIG. 1B. FIG. 11B depicts a portion of the coating having a homogeneous coating thickness covering the struts of the stent with a relatively smooth coating layer. Accumulation of excess material on the outer circumferential surface of the stent was not observed and the coating looked uniform. Compared to stent #1 the coating seems more homogeneous especially on the outer circumferential surface and at the side faces of the struts and an increased roughness of the surface is visible.

Figure 11C:
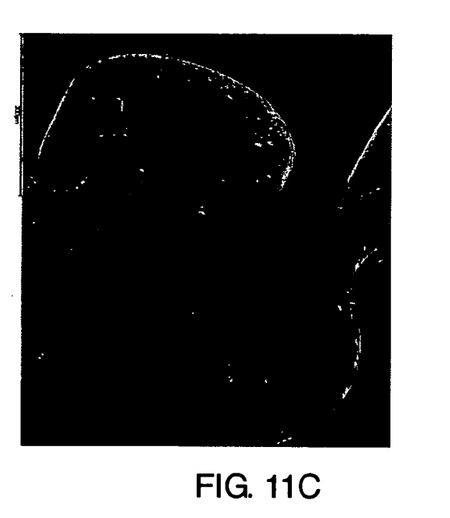
FIG. 11C is a SEM image of a portion of a stent at a swirl number of 0.6.

Stent #3 was coated at a swirl intensity of 0.6 according to the schematic representation of FIG. 1B. FIG. 11C illustrates a portion of a stent having a homogeneous thickness at the outer surface and at the side faces of the struts. Accumulation of excess material on the outer circumferential surface of the stent was not observed and the coating looked uniform. Compared to stent #1 and #2 an increased surface roughness and surface area is visible.

The difference between these stents is the thickness of the coating, with the coating on stent #1 being the thickest and with an inhomogeneous coating accumulation on the outer circumferential surface of the stent. The coating seems to be more homogeneous in terms of thickness with increased swirl numbers. In addition, the morphology in terms of roughness changes and a substantially increased surface area is noted at relatively high swirl intensities. Inducing a tangential velocity component in the gas stream by increasing the swirl intensity seems to improve process stability. This may result from an improved droplet break up and mixing of the coating composition leading to a more homogeneous droplet distribution. It was also observed that increased swirl intensities might prevent clogging of the atomizer.

Example II

Figure 12A:
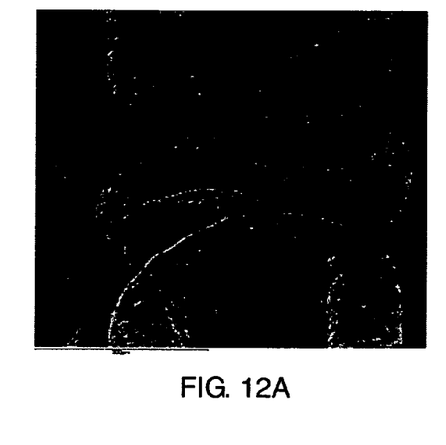
FIG. 12A is a SEM image (magnification 150×) showing the surface morphology of a portion of a stent.
Figure 12B:
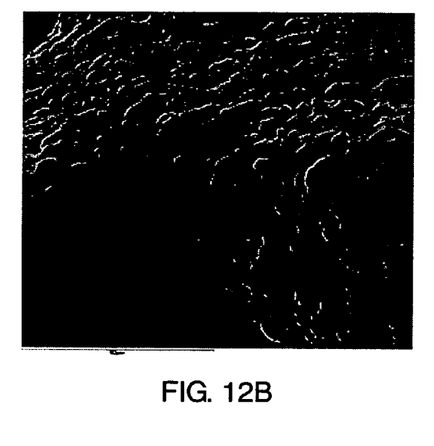
FIG. 12B is a SEM image (magnification 1000×) showing the surface morphology of a portion of a stent.
Figure 12C:
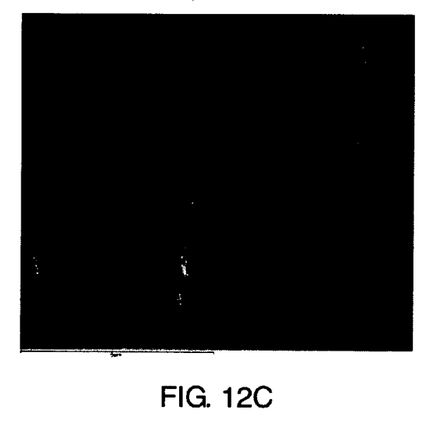
FIG. 12C is a SEM image (magnification 10000×) showing the surface morphology of a portion of a stent.

Several stents were coated according to the process of the present invention using the poly(tetrafluoroethylene) dispersion PTFE 307A (DuPont, Wilmington, Del., USA). The dispersion contains approximately 60% (by total weight) of 0.05 to 0.5 μm c resin droplets suspended in water and approximately 6% (by weight of PTFE) of a nonionic wetting agent and stabilizer. Both the inside and the outside surfaces of the stents were coated. The stents were coated at a swirl intensity of 0.3 according to the schematic representation of FIG. 1B. FIGS. 12A-C are scanning electron microscope (SEM) images of the coating morphology produced on a stent according to the process of the present invention at various magnifications.

Referring to FIG. 12A, a stent having a homogeneous coating with a comparatively large surface area and roughness is shown. Accumulation of excess material on the surface of the stent was not observed and the coating looked uniform.

To better visualize the morphology of the coating two further SEM images were taken. In FIG. 12B a small portion of the stent having an increased surface roughness and surface area is depicted at a magnification of 1000×. In addition, the image reveals the presence of pores.

FIG. 12C shows the portion of the stent at a magnification of 10000× to better visualize the morphology of the coating and to show the pores in more detail.

The different types of coatings exhibit a variety of properties with respect to the surface area, porosity and thickness of the coating. It has been found that the surface properties can be varied during the process by controlling the impact angle of the droplets with respect to the substrate to be coated. A more homogeneous coating having increased surface area, roughness and porosity can be obtained by increasing the tangential velocity component of the droplets. In contrast, when spraying higher viscosity polymer compositions without inducing a tangential velocity component the coating tends to accumulate at the outer circumferential surface of the stent which may result in coating defects such as webbing and peeling.

What is claimed is:

1. A method to apply a coating to a substrate using means to disintegrate the coating composition including at least a volatile and a nonvolatile component into droplets, comprising the steps of:
   generating a vortical gas flow field with a defined swirl intensity;
   forming droplets from the coating composition;
   transporting the droplets in said gas flow field to the substrate so that the majority of the droplets have a tangential velocity component in relation to the surface of the substrate; and
   depositing the droplets on the substrate so that a majority of the droplets have an impact angle of less than 80 degrees, whereby a coating with a desired surface morphology is produced by adjusting the swirl intensity of said vortical gas flow field.

2. The method according to claim 1, wherein the substrate is an implant.

3. The method according to claim 2, further including the step of tilting the means to disintegrate the coating composition in relation to the implant so that the majority of the droplets have an impact angle of less than 80 degrees on the surface of the implant.

4. The method according to claim 3, further comprising the step of changing the angle between a spray axis and the surface of the implant during the coating process in order to vary the morphology of the coating layer.

5. The method according to claim 1, wherein the means to generate a vortical gas flow field comprise a conduit with at least a first and a second gas inlet and at least one gas inlet is used to induce swirl motion in the gas flow.

6. The method according to claim 1, wherein the coating composition is disintegrated by the vortical gas flow.

7. The method according to claim 6, wherein the means to disintegrate the coating composition and to generate the vortical gas flow is a gas-assisted atomizer.

8. The method according to claim 1, wherein the swirl intensity can be changed by adjusting the ratio between the axial gas flux of swirl momentum and the axial gas flux of axial momentum.

9. The method according to claim 1, further comprising the step of changing the swirl intensity during the coating run in order to vary the morphology of the coating along the surface of the substrate.

10. The method according to claim 1, wherein the swirl intensity of the gas flow field, which is defined as a number representing axial flux of swirl momentum divided by axial flux of axial momentum and multiplied by the nozzle radius, is between 0.01 and 1.0.

11. The method according to claim 1, wherein the substrate is a stent and a homogeneous coating is obtained around the struts of the stent.

12. The method according to claim 1, wherein the coating composition may comprise a solvent, a polymer, and a therapeutic substance.

13. The method according to claim 12, wherein the diffusion rate of the therapeutic substance through the coating is controlled by changing the morphology of the coating.

14. A method to apply a coating to a substrate using means to disintegrate a coating composition including at least a volatile and a nonvolatile component and means to generate a gas flow field, the means to disintegrate the coating composition having an exit aperture and the means to generate the gas flow having an entrance aperture, comprising the steps of:
   generating droplets from the coating composition;
   generating a gas flow field;
   positioning the substrate between the exit aperture of the means to disintegrate the coating composition and the entrance aperture of the means to generate the gas flow;
   transporting the droplets to the substrate so that the majority of the droplets comprise a tangential velocity component in relation to the surface of the substrate; and
   depositing the droplets on the substrate so that a majority of the droplets have an impact angle of less than 80 degrees whereby a coating with a desired surface morphology is produced.

15. The method according to claim 14, wherein the gas flow field is generated by means of a suction device.

16. The method according to claim 14, wherein the substrate is supported by a fixture and the entrance aperture is located within the fixture.

17. The method according to claim 14, wherein the entrance aperture is positioned at an offset distance from a spray axis of the droplet generation device.

18. The method according to claim 17, wherein the position of the entrance aperture can be changed during the application of the coating to vary the morphology of the coating layer.

19. The method according to claim 14, wherein the entrance aperture is tilted in relation to a spray axis.

20. The method according to claim 14, wherein the droplets have a velocity of less than 5 m/s in proximity of the exit aperture.

21. A method to apply a coating to an implant, comprising the steps of:
generating droplets from a coating composition comprising at least a volatile and a nonvolatile component;
generating a gas flow field whereby a defined tangential velocity component is induced into the droplets;
transporting the droplets to the implant so that the majority of the droplets have a tangential velocity component in relation to the surface of the implant; and
depositing the droplets on the implant so that a majority of the droplets have an impact angle of less than 80 degrees whereby a coating with a desired surface morphology is produced
and,
wherein a majority of the droplets is generated through said vortical gas flow.

* * * * *